United States Patent
Poppleton

(10) Patent No.: US 7,114,851 B2
(45) Date of Patent: Oct. 3, 2006

(54) METHODS AND SYSTEMS FOR CALIBRATING MEDICAL IMAGING DEVICES

(75) Inventor: Kenneth Allen Poppleton, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 35 days.

(21) Appl. No.: 10/805,039

(22) Filed: Mar. 19, 2004

(65) Prior Publication Data

US 2005/0207539 A1    Sep. 22, 2005

(51) Int. Cl.
*G01D 18/00* (2006.01)
(52) U.S. Cl. .................... 378/207; 250/252.1
(58) Field of Classification Search ............... 378/207; 313/530, 542, 544, 103 CM, 104; 250/252.1, 250/214 VT, 214 LA
See application file for complete search history.

(56) References Cited

U.S. PATENT DOCUMENTS

| | | | | |
|---|---|---|---|---|
| 4,525,376 A | * | 6/1985 | Edgerton | 427/10 |
| 4,960,608 A | * | 10/1990 | Vieux et al. | 427/10 |
| 6,028,314 A | * | 2/2000 | Finkler | 250/370.11 |
| 6,086,252 A | * | 7/2000 | Quadflieg et al. | 378/207 |
| 6,194,700 B1 | * | 2/2001 | Pradere et al. | 250/214 VT |
| 6,476,394 B1 | * | 11/2002 | Amitani et al. | 250/368 |
| 6,960,879 B1 | * | 11/2005 | Koch et al. | 313/530 |

* cited by examiner

*Primary Examiner*—Edward J. Glick
*Assistant Examiner*—Jurie Yun
(74) *Attorney, Agent, or Firm*—Small Patent Law Group; Dean D. Small

(57) ABSTRACT

A method and system for calibrating medical imaging devices is provided. The method includes generating a calibration image within an X-ray imaging system and determining an image distortion of the X-ray imaging system based upon the calibration image for calibrating the X-ray imaging system.

22 Claims, 4 Drawing Sheets

METHODS AND SYSTEMS FOR CALIBRATING MEDICAL IMAGING DEVICES

BACKGROUND OF THE INVENTION

This invention relates generally to medical imaging systems, and more particularly, to methods and systems for calibrating X-ray medical imaging devices.

Diagnostic medical imaging requires accurate positioning of imaging equipment in relation to a patient. Further, proper calibration of the diagnostic medical imaging equipment is also required. Some diagnostic medical imaging systems are capable of movement, for example, from one room to another. For example, X-ray systems having wheels or other similar members for moving the system are known.

Distortions within an X-ray diagnostic medical imaging system may be caused by the X-ray system geometry, such as the geometry of an image intensifier. These distortions are static and may be corrected using, for example, models instead of calibration methods as are known. Such distortion may include, for example, pin cushion distortion caused by the curved surface of the image intensifier. Further, dynamic distortion of an X-ray image produced by such a system may be caused by interaction of the earth's and external magnetic fields with the electron paths within the image intensifier resulting in S-distortion. For example, these external distortions may be caused by surrounding factors such as structural elements (e.g. I-beams) carrying magnetic fields, other diagnostic medical imaging equipment operating nearby, such as, for example a magnetic resonance imaging (MRI) system and/or any other external source that may result in a change of the magnetic field surrounding the diagnostic medical imaging system.

For mobile X-ray systems, the dynamic nature of the distortion caused by the magnetic fields cannot be corrected through a static calibration. For example, when moving a mobile X-ray diagnostic medical imaging system from one room to another, non-uniform magnetic fields affecting the system may change.

Known methods provide for distortion correction of diagnostic medical imaging systems. For example, it is known to shield the image intensifier to minimize distortion. Other methods are known that provide active feedback to null out the earth's magnetic fields around the image intensifier using a sensor to measure the magnetic field and correct for changes in the magnetic field around the image intensifier. For fixed systems, other methods are known for measuring the magnetic fields off line and compensating for the magnetic field one time.

These known methods and systems for calibrating and/or correcting for distortion may have undesirable impacts or limitations. For example, shielding in the image intensifier may partially block x-rays being measured and result in a need for higher x-rays doses to image a patient. Further, active feedback is limited to providing correction for changes in a uniform or near uniform magnetic field depending on the number of sensors used. Additionally, off line measurements cannot correct for time varying magnetic fields relative to the x-ray system, such as are caused, for example, when the x-ray system is moved from one room to another.

BRIEF DESCRIPTION OF THE INVENTION

In one exemplary embodiment, a method for calibrating an X-ray imaging system is provided. The method includes generating a calibration image within an X-ray imaging system and determining an image distortion of the X-ray imaging system based upon the calibration image for calibrating the X-ray imaging system.

In another exemplary embodiment, a system for determining distortion within a X-ray imaging device is provided. The system includes a calibration image source within an image intensifier to generate a calibration image for use in determining distortion within the X-ray imaging device.

DETAILED DESCRIPTION OF THE INVENTION

Exemplary embodiments of systems and methods for calibrating medical imaging systems, and in particular X-ray imaging systems, are described in detail below. A detailed description of an exemplary medical imaging system, and specifically an X-ray imaging system, will first be provided followed by a detailed description of various embodiments of methods and systems for calibrating an image intensifier of such X-ray imaging systems.

Figure 1:
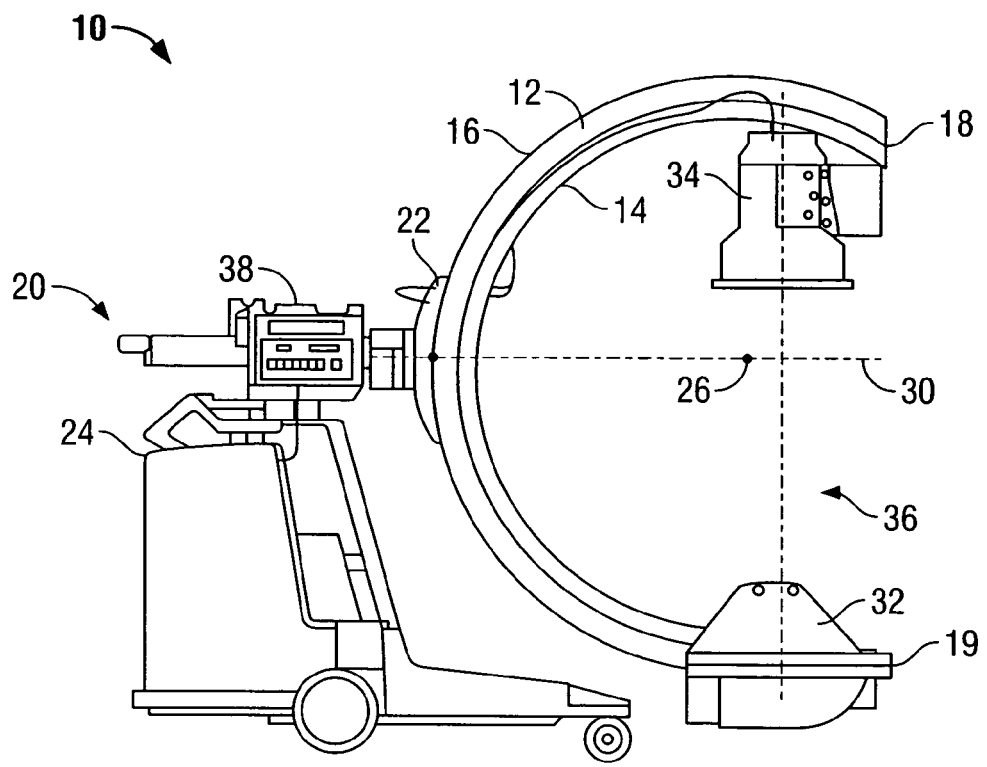
FIG. 1 is a side elevation view of a mobile C-arm X-ray imaging system in accordance with an exemplary embodiment of the present invention.

FIG. 1 is an exemplary embodiment of a diagnostic medical imaging system, and in particular, a mobile C-arm X-ray imaging system 10 in connection with which various embodiments of the present invention may be implemented. It should be noted that the various embodiments of the present invention may be implemented in connection with other types of medical imaging systems, including, in general, any type of medical imaging system subject to changing magnetic fields, particularly changing non-uniform magnetic fields. The C-arm X-ray imaging system 10 generally includes a C-arm support 12 having inner and outer circumferences 14 and 16, respectively, and terminating in opposing upper and lower distal ends 18 and 19. The C-arm support member 12, in the exemplary embodiment, has a uniform C-shape, but may include any arc-shaped member. Further, other configurations of mobile X-ray imaging systems may be provided (e.g., support arm positionable over a patient bed).

The C-arm support 12 is maintained in a suspended position by support means such as a support member 20, which may include a support arm 22 mounted upon a wheeled base 24. The support arm 22 provides rotational movement of the C-arm support 12 about an axis of lateral rotation 30, for example, with a bearing assembly (not shown) between the support arm 22 and C-arm support 12, or by the support arm 22 itself being rotatably mounted with respect to the wheeled base 24.

The wheeled base 24 enables transport of the C-arm X-ray imaging system 10, for example, from a first location to a second location including from a first room to a second room in a hospital. As such, the wheels of the wheeled base 24 operate as transporting means coupled to the support member 20 for transporting the support arm 22 and C-arm support 12 from a first location to a second location, for example when it may be desirable to move X-ray equipment from one room to another. The mobile nature of the C-arm X-ray imaging system 10 as provided by the wheeled base 24 offers, for example, increased access by patients in many different rooms of a hospital.

The support arm 22 is slideably mounted to the outer circumference 16 of the C-arm support 12 and the support member 20 includes means, such as structure and mechanisms to enable selective, sliding orbital motion of the C-arm support 12 about an axis of orbital rotation 26 to a selected position. The axis of orbital rotation 26 may coincide with a center of curvature of the C-arm support 12 and with an axis of lateral rotation 30. It will be appreciated that the sliding orbital motion causes the C-arm support 12 to move through various sliding points of an attachment (not shown) to the support arm 22. The support member 20 further includes means, such as mechanisms for laterally rotating the support arm 22 selectable amounts about the axis of lateral rotation 30 to a selected lateral position. The combination of sliding orbital motion and lateral rotation enables operation of the C-arm support 12 in two dimensions or degrees of movement (e.g., about two perpendicular axes). Thus, in operation, the C-arm X-ray imaging system 10 is provided with spherical moveability of the C-arm support 12. For example, the sliding orbital motion and lateral rotation enable an X-ray source 32 coupled to the C-arm support 12 to be moved to substantially any latitude/longitude point on a lower hemisphere of an imaginary sphere about which the C-arm support 12 is moveable.

The C-arm X-ray imaging system 10 includes the X-ray source 32 and an image receptor 34 as known generally in the X-ray diagnostic art, mounted upon opposing locations, respectively, on the C-arm support 12. The X-ray source 32 and image receptor 34 may be referred to collectively as an X-ray source/image receptor. As described in more detail herein, the image receptor 34 may be an image intensifier, or other light enhancing member. The orbital and laterally rotational manipulation of the C-arm support 12 enables selective positioning of the X-ray source 32 and image receptor 34 with respect to the width and length of a patient located within an interior space 36 of the C-arm support 12. Specifically, the C-arm X-ray imaging system 10 may include a servo system (e.g., a digital/electrical/mechanical system that performs mechanical movement under software control, which may use feedback) coupled to a controller 38. The sliding orbital movement of the C-arm support 12 causes the X-ray source 32 and image receptor 34 to move along respective arcuate paths. In one exemplary embodiment, the image receptor 34 is secured to the inner circumference 14 of the C-arm support 12 and the X-ray source 32 also may be secured to the inner circumference 14.

It should be noted that as used here in, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

It also should be noted that additional or different component parts may be provided as part of the C-arm X-ray imaging system 10. For example, the C-arm X-ray imaging system 10 may include a table for supporting a patient within the space 36. In operation, to generate an image of the patient, the C-arm support 12 is rotated to move the X-ray source 32 and image receptor 34 about the patient. Specifically, the C-arm support 12 is rotatably coupled to the support member 20 such that the X-ray source 32 and image receptor 34 are rotated about the patient or other object to be imaged.

Figure 2:
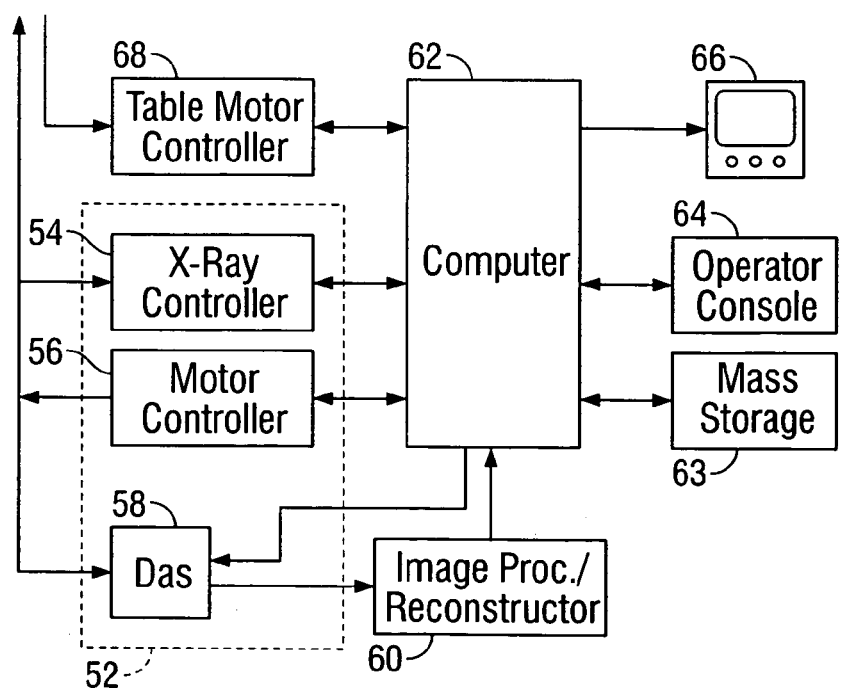
FIG. 2 is a block diagram of a control system for controlling the C-arm X-ray imaging system shown in FIG. 1.

As shown in FIG. 2, movement of the C-arm support 12 and the operation of the X-ray source 32 and image receptor 34 are controlled by a control mechanism 52 of the C-arm X-ray imaging system 10, which may be provided as part of the controller 38 (shown in FIG. 1). The control mechanism 52 generally includes an X-ray controller 54 that provides power and timing signals to the X-ray source 32 and a motor controller 56 that controls the position of the C-arm support 12, X-ray source 32 and image receptor 34.

In an exemplary embodiment, a data acquisition system (DAS) 58 provided as part of control mechanism 52 samples data from the image receptor 34, such as an X-ray detector, for subsequent processing. An image processor/reconstructor 60 receives sampled X-ray data from the DAS 58 and performs image processing/reconstruction. Resultant images are provided as an input to a computer 62 that may store the images in a mass storage device 63 (e.g., disk storage). It should be noted that the term reconstructor as used here includes reconstructors as are known in the medical imaging art, as well other suitable processes for processing data collected in a scan.

The computer 62 also receives commands and scanning parameters from an operator via a console 64 that includes a user input, such as, for example a keyboard. One or more displays 66 allow the operator to observe the resultant image and other data from the computer 62. Operator supply commands and parameters are used by the computer 62 to provide control signals and information to the DAS 58, X-ray controller 54 and motor controller 56. The computer 62 also operates a table motor monitor 68 that may control the position, for example, of a motorized table (not shown) relative to the C-arm X-ray imaging system 10 (shown in FIG. 1).

Figure 3:
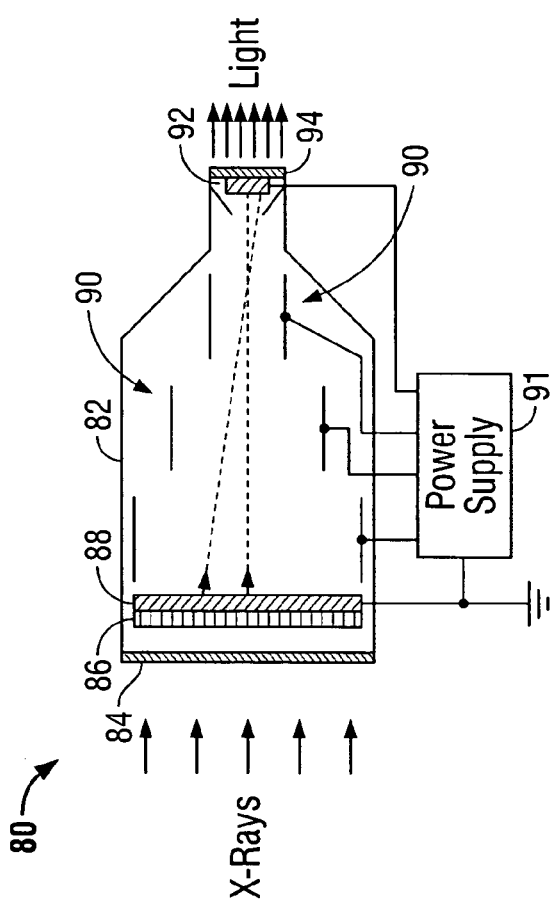
FIG. 3 is a schematic illustration of an image intensifier in accordance with an exemplary embodiment of the present invention.

As shown in FIG. 3, an X-ray image intensifier 80 may be provided as part of the C-arm X-ray imaging system 10, and more particularly, configured as an image receptor, to increase the intensification (e.g., brightness) of X-ray images. The X-ray image intensifier 80 includes a generally cylindrically-shaped body having components provided within a housing 82 provided in a vacuum. As shown in FIG. 3, an input screen or window 84 receives X-rays, for example immerging from a patient (generated by the X-ray source 32 shown in FIG. 1) and allow the X-rays to be exposed to an input phosphor 86. The input phosphor 86 scintillates and light photons strike a photocathode 88, which then emits electrons. The electrons are accelerated and focused by electron optics 90 on to an output phosphor 92 that emits light through an output screen or window 94. The light provides an image of the X-ray pattern that emerged, for example, from the patient and that has a substantially greater intensity than the originally received X-rays.

Specifically, and in one exemplary embodiment, the input window or screen 84 may be constructed of a thin sheet (e.g., 0.25–0.5 millimeters) of aluminum or titanium. The input phosphor 86 may be comprised of CsI, doped with Na that is deposited on an aluminum substrate. An intermediate layer (e.g., less than 0.001 millimeter thick) is evaporated onto the inner surface of the input phosphor 86 and a photocathode 88 is deposited on this layer. In operation, the vacuum sealed housing 82, such as an image intensifier tube, operates using a voltage of for example twenty-five to thirty-five kilovolts (kV) from a power supply 91 to accelerate the electrons. The electron optics 90 are used for focusing the electrons onto the output phosphor 92. A current of about, for example, $10^{-8}$ to $10^{-7}$ may also be provided and results in the acceleration of focusing electrons that results in image intensification. It should be noted that image magnification may be achieved by varying the voltages on the electrodes of the electron optics 90. The output phosphor 92 may comprise ZnCdS Ag deposited on the output screen or window 94. A thin aluminum film may be provided on the inner surface of the output phosphor 92. The output window or screen 94 may include a glass window (e.g., 15 mm thick window) with external anti-reflection layers, tinted glass window and a fiber optic window. The resulting image produced by the light through the output window or screen 94 may be viewed by various camera.

Figure 4:
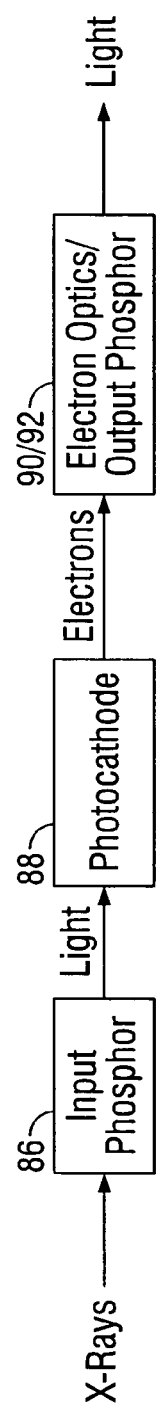
FIG. 4 is a block diagram illustrating the operation of the image intensifier shown in FIG. 3.

Thus, in operation, as is shown in FIG. 4, X-rays are converted to light by the input phosphor 86, which light is then converted to electrons by the photocathode 88 and thereafter converted to an intensified light by the electron optics 90 and output phosphor 92.

Figure 5:
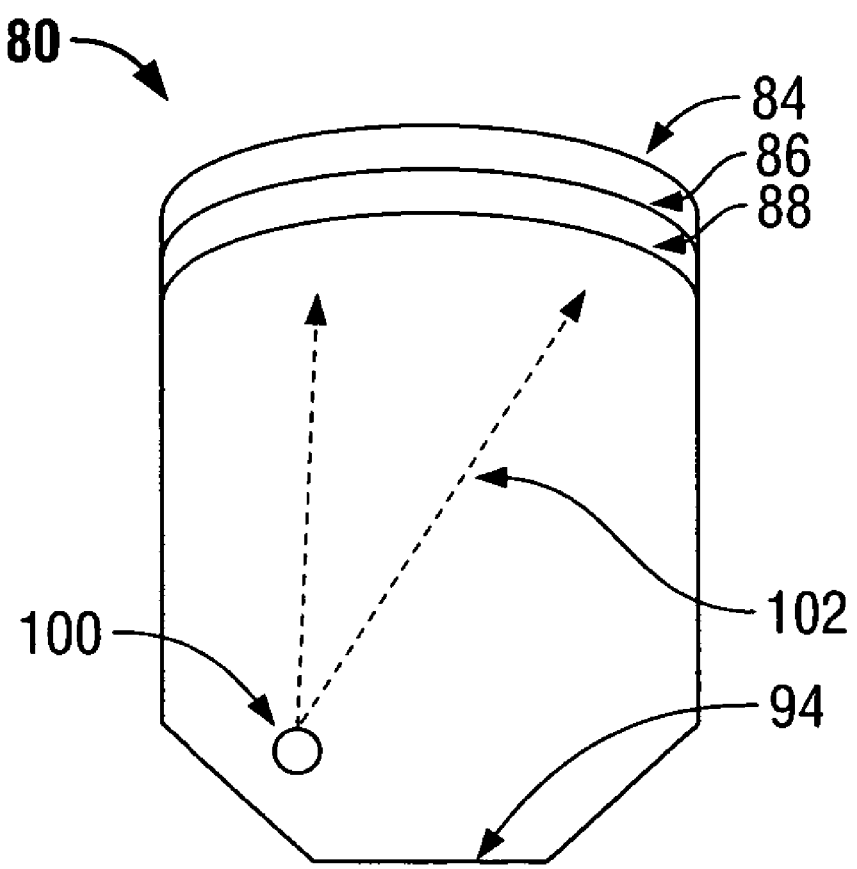
FIG. 5 is a schematic diagram illustrating the generation of a calibration image within an image intensifier in accordance with an exemplary embodiment of the present invention.

Various embodiments of the present invention dynamically measure image intensifier distortion and allow for correction thereof. In general, and as shown in FIG. 5, a calibration image source 100 is provided within the X-ray image intensifier 80 generally at an end of the X-ray image intensifier 80 that is closer to the output window or screen 94 than to the input window or screen 84, which in an exemplary embodiment is an aluminum element. The calibration image source 100 generates optical light rays 102 that are projected back towards the photocathode 88 overlaid on the input phosphor 86, which may be a florescent screen, and which causes the generation of electrons by the photocathode 88. The electrons are then converted to light by the electron optics 90 and output phosphor 92 (shown in FIG. 3) as described herein.

Figure 6:
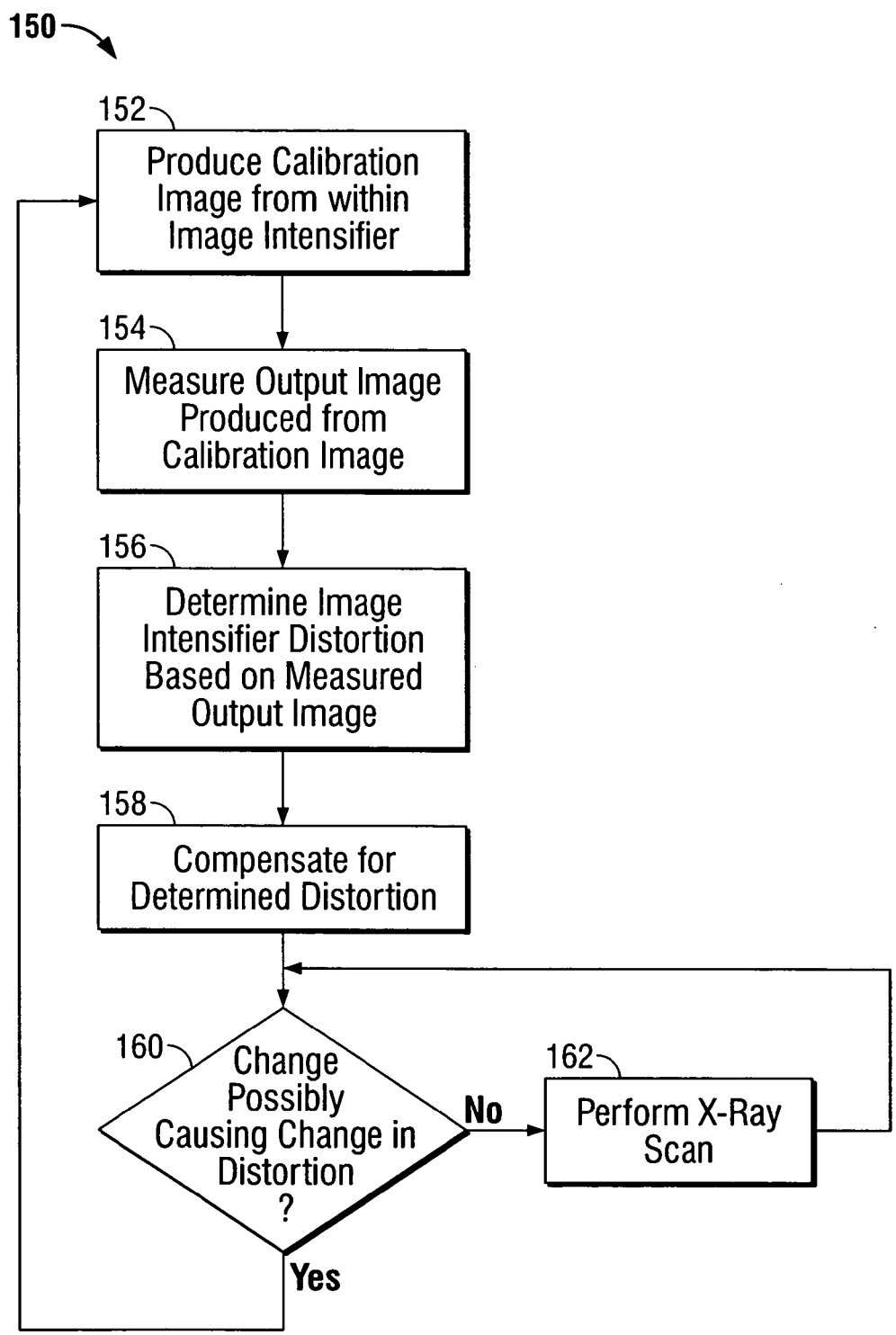
FIG. 6 is a flow chart of an exemplary method for calibrating an image intensifier in accordance with an exemplary embodiment of the present invention.

Specifically, an exemplary embodiment of a method or process 150 for dynamically measuring image intensifier distortion is shown in FIG. 6. In particular, at 152 a calibration image is generated from within the image intensifier 80 (shown in FIG. 3) by the calibration image source 100 (shown in FIG. 5). The calibration image may be any generated pattern that may be identified and/or measured, for example, a grid, dots, pattern of shapes, such as triangles, or other identifiable and measurable pattern. It should be noted that the calibration image source 100 may be any suitable device for generating such a pattern, such as, for example a laser within the image intensifier 80. The light pattern striking the photocathode 88 produces electrons as described herein and the output image generated from the calibration image is measured at 154. Specifically, the output image may be compared to the calibration image produced at 152 to determine differences, for example, distortion in the image. For example, if the calibration image is a grid, the cross points of lines may be measured, for example a measure in the shift. Thus, and for example, by measuring the distorted grid as compared to the original grid produced by the calibration image source 100, a determination of the image intensifier distortion is made at 156. Specifically, the image intensifier distortion, for example that may be caused by external non-uniform magnetic fields, is measured. The determined distortion then may be compensated at 158, for example, as is know, using bi-linear interpolation or surface interpolation to generate a non-distorted image.

Thereafter a determination is made at 160 whether a change may have occurred causing a change in the distortion, for example, whether a regularly scheduled maintenance is required, whether the C-arm X-ray imaging system 10 (as shown in FIG. 1) has been moved, if maintenance has been performed on the C-arm X-ray imaging system 10 or whether some other external or exterior source may be causing distortion (e.g., operation of another medical imaging system, such as an MRI system in another room). If no change has occurred, then at 162 an X-ray scan may be performed using the calibrated C-arm X-ray imaging system 10 (as shown in FIG. 1). If a change in an external source that may cause change in the distortion is determined to be present, then the calibration image is produced at 152 and thereafter followed by the other operations in the method 150.

Thus, for example, the various embodiments of the present invention may be used iteratively between X-rays or performed after a diagnostic medical imaging system has been moved to compensate for changes in external magnetic fields (e.g., non-uniform magnetic fields). However, it should be noted that the various embodiments described herein may be performed as often as needed or desired. For example, various embodiments described herein may be performed after each scan of a patient using the C-arm X-ray imaging system 10.

The various embodiments of the present invention may be modified as desired or needed. For example, various component parts for generating the calibration image as described herein may be modified. For example the calibration source 100 within the image intensifier 80 may be a light source, such as a laser with a diffraction grating used to produce the pattern defining the calibration image. In other embodiments, several light sources distributed throughout the interior of the image intensifier 80 may be used to produce the pattern defining the calibration image. In still other embodiments, the pattern may be produced by creating a shadow pattern through the blocking of a flood illumination. This may be provided, for example, by applying to the inside of the photocathode 88 a material that is optically opaque and transparent to electrons and illuminating the interior of the X-ray image intensifier 80 with a light source.

Thus, the various embodiments of the present invention provide distortion measurement independent of X-ray generation and detection and allow, for example, for measurement of image intensifier distortion between X-ray pulses (e.g., dynamic measurement). The various embodiments allow for measurement of image intensifier distortion at any time, for example with a patient on the exam table, and do not require off-line calibration of the image intensifier distortion. Further, the pattern defining the calibration image may be a known pattern or a measured pattern. Further, the distortion measurement and correction may be applied to all images from an X-ray system. Also, the pattern defining the calibration image source does not change with orientation or time. Additionally, distortion correction between two samplings of the correction image pattern may be interpolated to determine a more accurate distortion correction for an X-ray projection taken between two correction images. Thus, a projected optical pattern from inside the image intensifier used to stimulate a photocathode, or any other means for stimulating a pattern in the photocathode without the use of X-ray allows for direct measurement of image intensifier distortion.

While the invention has been described in terms of various specific embodiments, those skilled in the art will recognize that the invention can be practiced with modification within the spirit and scope of the claims.

What is claimed is:

1. A method for calibrating an X-ray imaging system, said method comprising:
   configuring an output of a calibration image source in a pattern to define a calibration image;
   generating a calibration image within an X-ray imaging system using the calibration image source only in the absence of X-rays; and
   determining an image distortion of the X-ray imaging system based upon a plurality of samplings of the calibration image for calibrating the X-ray imaging system.

2. A method in accordance with claim 1 further comprising calibrating the X-ray imaging system using the calibration image.

3. A method in accordance with claim 2 wherein the calibrating is performed after one of determining a change in an external source causing distortion and moving the X-ray imaging system.

4. A method in accordance with claim 1 wherein the X-ray imaging system comprises an image intensifier and the generating is performed within the image intensifier.

5. A method in accordance with claim 1 further comprising measuring an output image generated based upon the calibration image to determine the image distortion.

6. A method in accordance with claim 1 wherein the calibration image comprises a pattern.

7. A method in accordance with claim 6 wherein the pattern comprises one of a grid, a plurality of dots and a pattern of shapes.

8. A method in accordance with claim 1 wherein the generating a calibration image comprises generating a light pattern.

9. A method in accordance with claim 1 wherein the generating a calibration image comprises generating a non-X-ray pattern.

10. A method in accordance with claim 1 wherein the determining comprises comparing the calibration image to an output image to determine the image distortion.

11. A method in accordance with claim 1 wherein the calibration is performed in connection with a mobile X-ray imaging system to compensate for changes in non-uniform magnetic fields.

12. A method in accordance with claim 1 further comprising compensating for the image distortion.

13. A method in accordance with claim 1 wherein the X-ray imaging system comprises a calibration image source within an image intensifier for generating the calibration image within the image intensifier, the calibration image source positioned within the image intensifier generally at an end of the image intensifier that is closer to an output window than to an input window.

14. A method for determining distortion in an X-ray imaging system, said method comprising:
   generating a light pattern at an output of a calibration image source within an image intensifier of an X-ray imaging system;
   comparing to the light pattern output of the calibration image source a plurality of outputs produced by the image intensifier that are interpolated; and
   determining a distortion based upon the comparison.

15. A method in accordance with claim 14 further comprising compensating for the distortion.

16. A method in accordance with claim 14 wherein the light pattern comprises one of a measurable and identifiable pattern.

17. A method in accordance with claim 14 wherein the image intensifier comprises a calibration image source having at least one laser light source for generating the light pattern.

18. A method in accordance with claim 17 wherein the laser light source comprises a grating for creating the light pattern.

19. A system for determining distortion within an X-ray imaging device, said system comprising:
   a calibration image source within an image intensifier configured to generate a calibration image pattern at an output of the calibration image source for use in determining distortion within the X-ray imaging device based on a plurality of samplings of a correction image generated from the calibration image pattern only in the absence of X-rays.

20. A system in accordance with claim 19 wherein the calibration image comprises a pattern.

21. A system in accordance with claim 19 wherein the calibration image source is positioned within the image intensifier generally at an end of the image intensifier that is closer to an output window than to an input window, and directed generally towards the input window.

22. A system in accordance with claim 19 wherein the X-ray imaging system comprises a mobile X-ray imaging system.

* * * * *